US008218781B1

(12) United States Patent
Swanke

(10) Patent No.: US 8,218,781 B1
(45) Date of Patent: Jul. 10, 2012

(54) AUDIBLE FAN NOISE CANCELLATION

(75) Inventor: Christopher J. Swanke, Cedar Rapids, IA (US)

(73) Assignee: Rockwell Collins, Inc., Cedar Rapids, IA (US)

( * ) Notice: Subject to any disclaimer, the term of this patent is extended or adjusted under 35 U.S.C. 154(b) by 1216 days.

(21) Appl. No.: 11/821,281

(22) Filed: Jun. 22, 2007

(51) Int. Cl.
*A61F 11/06* (2006.01)
*G10K 11/16* (2006.01)
*H03B 29/00* (2006.01)

(52) U.S. Cl. ......................... 381/71.3; 318/41; 381/71.1

(58) Field of Classification Search ........ 381/71.1–71.9, 381/71.11–71.14, 94.1–94.9; 181/225, 206, 181/214, 213, 222, 224, 229; 318/41, 49, 318/67
See application file for complete search history.

(56) References Cited

U.S. PATENT DOCUMENTS 5,995,632 A * 11/1999 Okada .......................... 381/71.3
2005/0237717 A1* 10/2005 Babb et al. .................... 361/697
2006/0103334 A1* 5/2006 Abali et al. .................... 318/67

FOREIGN PATENT DOCUMENTS

JP 04-308397 * 10/1992

* cited by examiner

*Primary Examiner* — Xu Mei
*Assistant Examiner* — Lun-see Lao
(74) *Attorney, Agent, or Firm* — Donna P. Suchy; Daniel M. Barbieri

(57) ABSTRACT

The present examples provide for the cancellation, or substantial reduction, of fan noise typically encountered in equipment cooling applications. Local audio nulls may be created by adjusting fan velocity and/or phase to cancel the fan noise near an operator. In a first example, phase and velocity of the fan may be controlled by feedback techniques. This technique utilizes feedback provided by a microphone located in the proximity of the operator to create an area of audio nulling of the fan noise. Local audio nulls may also be created by manipulating fan, phase and velocity by a controller that implements a process to create local audio nulls using the fixed position of equipment and the operator in the determination.

19 Claims, 7 Drawing Sheets

AUDIBLE FAN NOISE CANCELLATION

TECHNICAL FIELD

This description relates generally to the cooling of heat generating mechanical or electronic equipment with cooling fans and more specifically to, the reduction or cancellation of noise generated by the cooling fans.

BACKGROUND

Many types of equipment, including electrical and mechanical equipment, typically generate undesired heat. Heat buildup in a mechanical assembly, such as an engine, or in an electronic assembly, such as a computer, can be a problem. Heat buildup typically prevents equipment from operating efficiently, and may also cause equipment failure by the seizing or binding of mechanical parts, and the failure of electronic parts due to various failure mechanisms.

Cooling of equipment typically includes a heat exchanger for heat transfer from the equipment being cooled to either air or liquid. Liquid may be pumped through the heat exchanger and air may be moved over to the heat exchanger by fans, convection or the like in an attempt to increase the rate of heat transfer. However, pumps and fans typically generate noise which may be undesirable to operators working or stationed near this equipment. Fans in particular, tend to produce high pitched loud noise levels.

Cooling fans are often used in cooling electronic equipment. Moving air has long been used as an efficient, and economical method of cooling electronics, without the need for complicated heat exchangers, pumps and liquid coolers and the like. However, fans tend to be noisy, making working near equipment cooled by fans unpleasant and possibly damaging to one's hearing.

An operator is typically located near the electronic equipment they are working with, such as a radio transmitter or other high powered device that typically generates a great deal of heat. High heat dissipating equipment is typically cooled by banks of cooling fans running at high speeds. A high speed fan typically generates large amounts of fan noise which may be undesirable to those working with the equipment or nearby. Thus, it may be desirable to minimize fan noise heard by an operator or other person located near the equipment being cooled with fans.

SUMMARY

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

The present examples provide for the cancellation, or substantial reduction, of fan noise typically encountered in equipment cooling applications. Local audio nulls may be created by adjusting fan velocity and/or phase to cancel the fan noise near an operator. In a first example, phase and velocity of the fan may be controlled by feedback techniques. The feedback techniques utilize feedback provided by a microphone located in the proximity of the operator to create an area of audio nulling of the fan noise. Local audio nulls may also be created by manipulating fan, phase and velocity by a controller that implements a process to create local audio nulls using the fixed position of equipment and the operator in the determination.

Many of the attendant features will be more readily appreciated as the same becomes better understood by reference to the following detailed description considered in connection with the accompanying drawings.

DESCRIPTION OF THE DRAWINGS

The present description will be better understood from the following detailed description read in light of the accompanying drawings, wherein.

Like reference numerals are used to designate like parts in the accompanying drawings.

DETAILED DESCRIPTION

The detailed description provided below in connection with the appended drawings, is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

The examples below describe a fan noise reduction. Although the present examples are described and illustrated herein as being implemented in an electrical system, the system described is provided as an example and not a limitation. As those skilled in the art will appreciate, the present examples are suitable for application in a variety of different types of electrical systems.

Figure 1:
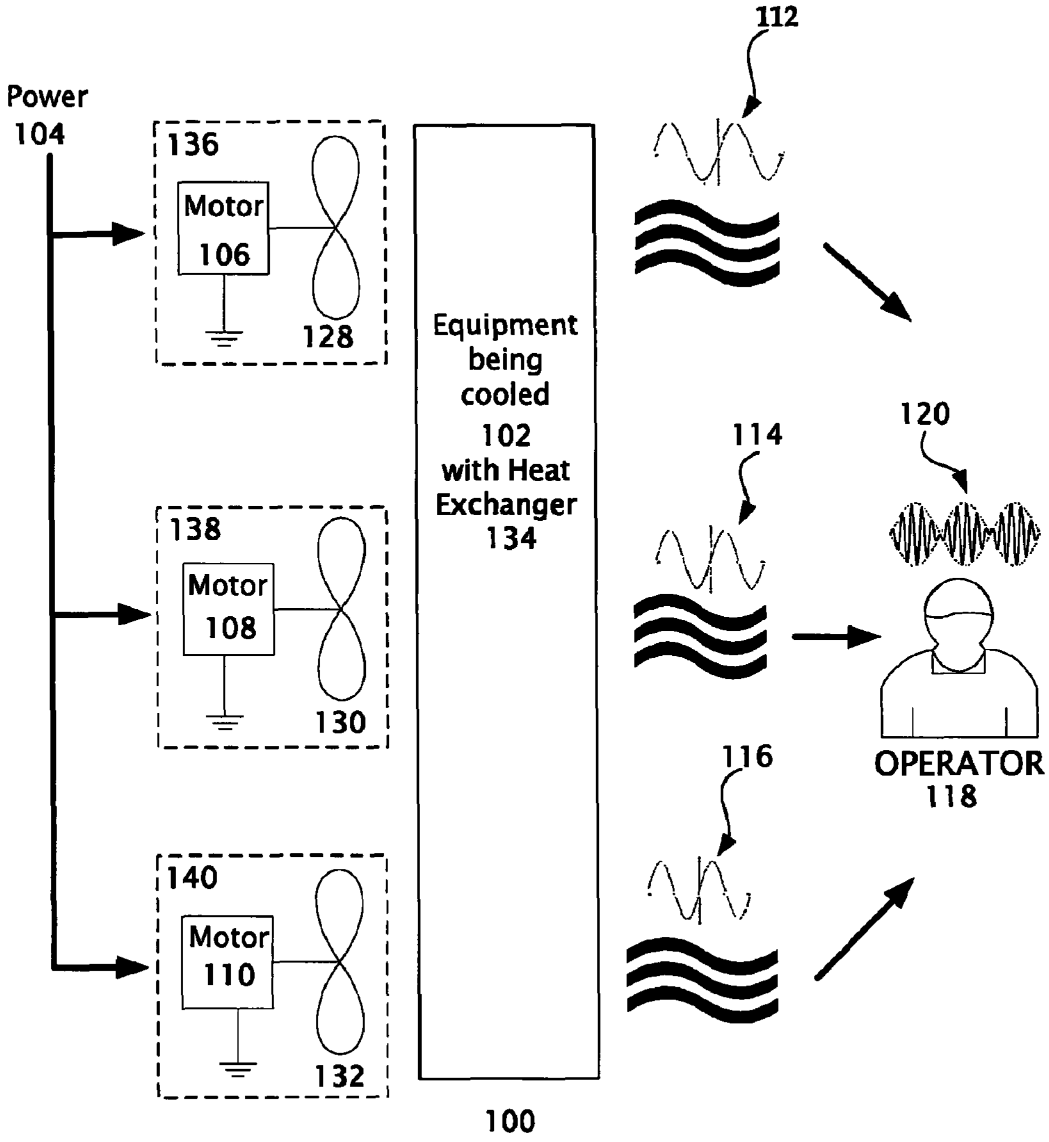
PRIOR ART FIG. 1
FIG. 1 shows a conventional electrical (or mechanical) equipment having cooling fans which generate noise heard by an operator.

FIG. 1 shows a conventional electrical (or mechanical) equipment having cooling fans which generate noise heard by an operator 100. In this typical cooling arrangement, AC or DC power 104 is typically applied to a plurality of conventionally constructing fans 136, 138 and 140 that blow air over a conventional heat exchanger 134 to cool the exemplary electronic equipment 102 coupled to the heat exchanger 134.

Fan 136 may include a typical motor 106 and conventionally constructed fan blade 128. Fan 138 includes a conventionally constructed motor 108 and a conventionally constructed fan blade 130. And finally, motor 140 may include a conventionally constructed motor 110 and a conventionally constructed fan blade 132. The fans, including the motors and blades, are typically similarly constructed so that the noise they generate tend to be alike, all other conditions such as, heat exchanger geometry being the same. The motors 106, 108 and 110 are not locked in synchronization to the applied power signal 104. Thus, it is possible for the rotation of the fan blades coupled to each motor to vary in speed causing differences in the noise of each fan which is heard by the operator 118.

Each of the fans 136, 138 and 140 typically generate acoustical noise 112, 114 and 116 that may be attributed to each of the fans as shown. If the fans are being supplied from a common power source and the fan is typically identical in construction, the noise profile 112, 114 and 116 are typically substantially equal in amplitude and phase. However, due to drift and finite differences in the construction of each of the fans, the noise profile may vary slightly in phase and amplitude. This phase and amplitude variation may result in a beating together of the individual noise signals 112, 114 and 116 to create a pulsating sound 120 heard by an operator 118. Alternatively, the noise signals may be sufficiently synchronized, and may not beat together. In this case, just a simple continuous loud noise may be heard by the operator 118. However, the fact that beating is heard tends to indicate that the noise heard by the operator at his work station, may be manipulated and perhaps cancelled or reduced.

Adjusting the phase and/or velocity of the fans may help reduce or eliminate noise 120 heard by an operator 118 if the fans can be synchronized so that noise signals 112, 114 and 116 generated by each fan tends to cancel when superimposed at the operator's work station, or location.

Figure 2:
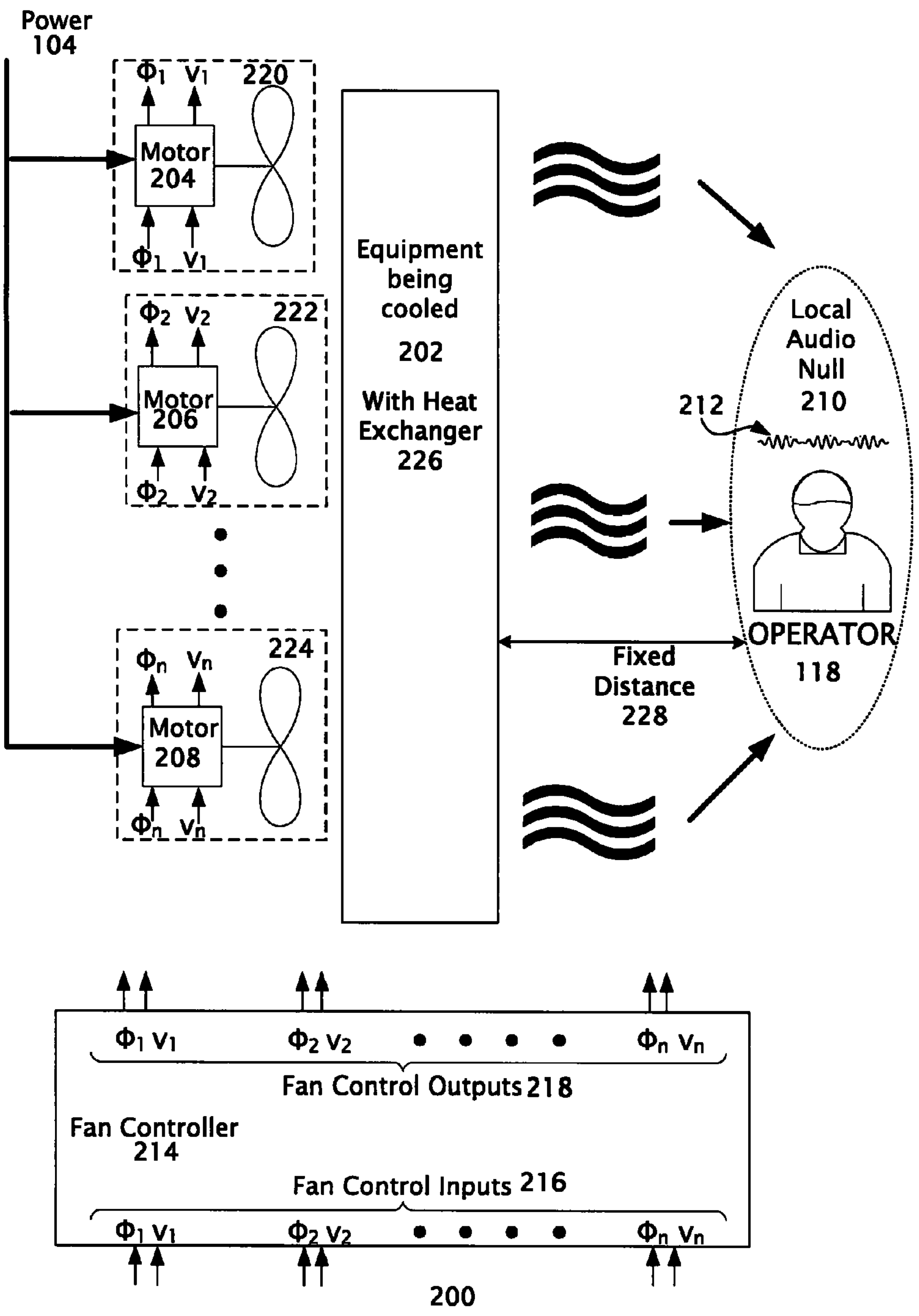
FIG. 2 is a block diagram of an example of equipment including audible fan noise cancellation, or reduction, that utilizes a fixed relative location to implement noise cancellation.

FIG. 2 in a block diagram of an example of equipment including audible fan noise cancellation, or reduction that utilizes a fixed distance 228 to implement noise cancellation 200. This example includes a plurality of fans 220, 222 and 224 that typically generate outputs indicating the velocity and phase of the fan. For example, fan motor 1204 generates phase and velocity outputs $\phi_1$ and $V_1$. Fan motor 2206 typically generates phase and velocity output $\phi_2$ and $V_2$ respectively. And finally, the nth fan motor 208 may generate phase and velocity output $\phi_n$ and $V_n$ respectively.

The motors 204, 206 and 208 are also shown as having control inputs. Control inputs may typically include phase and velocity controls. The phase and velocity controls may be included in the motor assembly as built or added on as an associated, and possibly separate, assembly. Motor 204 includes phase and velocity input control $\phi_1$, $V_1$. Motor 206 may include phase and velocity input $\phi_2$ and $V_2$ respectively. And finally, the nth motor 208 may include phase and velocity input $\phi_n$ and $V_n$. Each of the phase and velocity motor inputs are noted in the figure with arrows pointing to the respective motor. Each of the phase and velocity outputs from each fan motor are indicated by an arrow pointing away from the appropriate motor.

In this example, a conventional power source 104 is coupled to each of the fans 220, 222 and 224 to cool equipment 202 via a heat exchanger 226. In this example, an operator 118 is typically located a fixed distance 228 from the equipment 202. This distance may vary somewhat, and still maintain the desired noise cancellation, with the cancellation tending to degrade as one moves away from the prescribed distance. In an alternative example, not only distance, but location or angle away from a normal axis to the equipment may be used to determine cancellation.

Equipment operators or other people are often located in somewhat of a fixed distance, or position from noisy electronic equipment. Such a situation may occur in a trailer filled with communications gear where an operator or other personnel are seated a fixed distance from the equipment without a lot of room to move about. Another example, would be a person operating a piece of equipment who would usually be within arms length of the equipment so that they can operate it from the front panel. Thus, in these situations, the operator or other person would typically be in a general distance area that tends to be somewhat of a known distance 228 away from the equipment. In this example, the fans 220, 222 and 224 are adjusted such that a local audio null 210 tends to be produced in the operators work zone. A signal representing the reduced noise level 212 shown. The reduced noise level may be of any wave shape that tends to exhibit reduced acoustic energy heard by the operator 118.

A fan controller 214 utilizes the fixed distance 228 in order to control the fans 220, 222 and 214 to produce a local audio null 210. A plurality of fan control outputs 218 are coupled to fans 220, 222 and 224 to control fan velocity (V) and/or phase ($\phi$).

Any convenient number of fans may be controlled in this manner. Fan output control signals 218 may be conventional control signals of either an analog or digital nature. If an analog signal, information may be represented by a current, or a voltage. A plurality of fan control input signal 216 may also be supplied from the respective fans 220, 222 and 224 to the fan controller. The signals generated by the fans may be conventional analog or digital control signals. And again, if an analog signal, the signal information may be conveyed by a current or a voltage.

These fan control input signals 216 may or may not be utilized in generating a local audio null. They are optional and may be utilized in alternative examples of generating an audio null. However, in the example shown, they are optional as the fixed distance 228 may be used alone in this example to generate the local audio null.

The fan controller 214, controls the fan by taking into consideration the fan control inputs 216 and the fixed distance 228 of the operator 118 from the equipment 202 to generate the fan control outputs 218 such that a local audio null 210 is produced, and the noise level heard by the operator 118 tends to be reduced.

Figure 3:
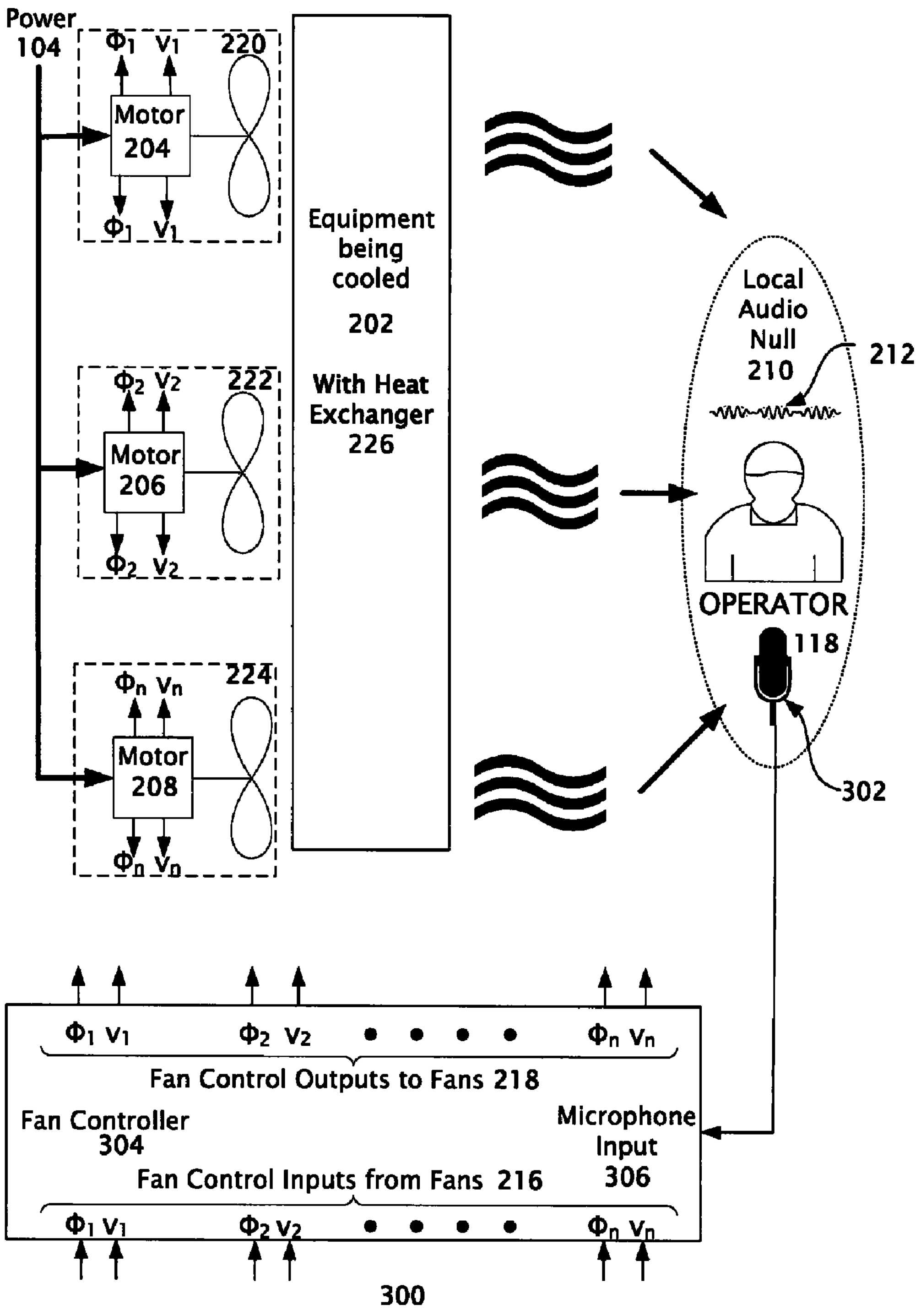
FIG. 3 shows an example of audio noise cancellation in which feedback from a microphone may be used to produce a local audio null.

FIG. 3 shows an example of audio noise cancellation in which feedback from a microphone 302 may be used to produce a local audio null 300. In this example, a microphone 302 is used as a feedback element. Instead of using a known distance of the operator 118 to the equipment 202 to generate a local audio null as previously described. This audio noise cancellation example tends to allow an operator to move about (with the microphone) to maintain noise cancellation. Also, this example allows for ease in calculation such as when the operator is not directly positioned in front of the fans.

Microphone 302 is conventionally constructed and typically placed near an operator 118, or other location where it may be desired to cancel or eliminate audible fan noise. The microphone 302 may be coupled to the fan controller 304 at a microphone input 306. The fan controller 304 may include conventionally constructed control loop circuitry to produce a plurality of fan control outputs 218. A plurality of fan control inputs 216 may be coupled to inputs of the control loop to contribution to the generation of the fan control outputs 218. The fans 220, 222 and 224 and the equipment being cooled 202, with the heat exchanger 226, are as previously described.

The fan controller 304 generates fan control outputs 218 which can be coupled to each fan. The fans velocity and/or phase are adjusted accordingly as instructed by the fan controller 304. Once a suitable local audio null 210 has been established as indicated by the signal produced in the microphone 302, the nulling operation may stop and the microphone may be removed. However, the microphone may be kept there with monitoring continuing and further adjustments made when conditions change.

Figure 4:
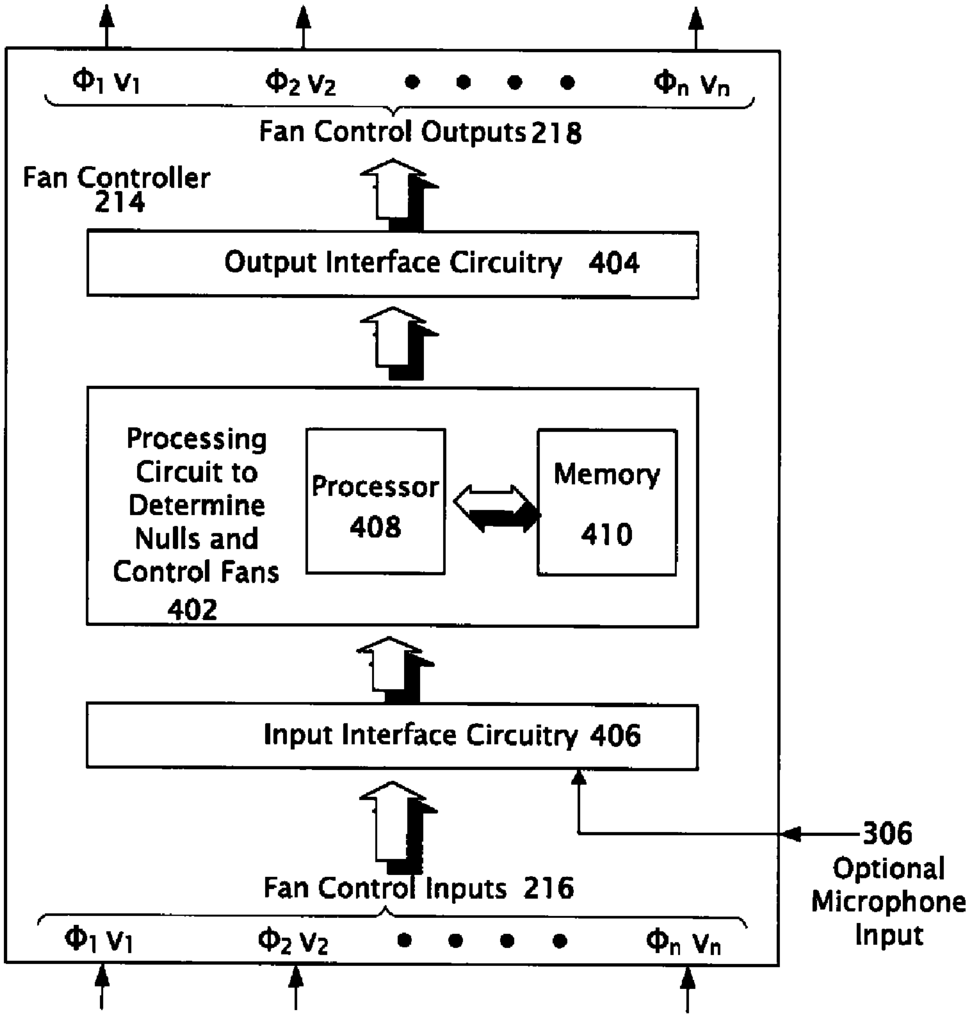
FIG. 4 is a block diagram of an example of a fan controller that may utilize a fixed distance (of FIG. 2) to calculate a plurality of fan control outputs.

FIG. 4 is a block diagram of an example of the fan controller 214 that may utilize a fixed distance (228 of FIG. 2) to calculate a plurality of fan control outputs 218. In the example shown, a plurality of fan control inputs 216 may be coupled to conventionally constructed input interface circuitry 406, such that, digital signals may be generated and coupled to processing circuitry to determine nulls and control the fans 402.

As an alternative example, an optional microphone input 306 may be utilized in sensing the null. As shown, the optional microphone input 306 may be coupled to the input interface circuitry 406 for processing into a control signal type suitable for use by the processing circuitry to contribute to determining nulls and controlling the fans 402.

The processing circuitry to determine nulls and control fans 402, typically includes a conventional processor 408 coupled to outputs from the input interface circuitry 406. The processor 408 works in conjunction with a conventional memory 4102 produced fan control outputs. The digital fan control outputs may then be coupled to the output interface circuitry 404. The fans may be controlled directly by the signals from the processing circuitry 402, however, the output interface circuitry 404 may be used to augment the signal or drive levels as desired.

The processing circuitry to determine nulls and control fans 402, typically executes a conventional process for determining nulls. In this process, the position of the equipment relative to the operator, including the distance between the operator and the equipment is taken into account, as well as the fan control inputs providing phase and velocity information regarding the current state of the fans to produce suitable fan control outputs 218. The operators angle away from moral to the fans may also be taken into account in the determination. The processing circuitry may also be implemented as a DSP dedicated programmable gate array or the like.

The output interface circuitry 404 is conventionally constructed and suitable for converting digital signals generated by the processing circuitry to determine nulls and control fans 402 into suitable control signals output as a plurality of fan control outputs 218. Fan control outputs may be analog or digital signals. If an analog, the signal may be current or voltage based control signals.

In a further alternative example, an optional microphone input 306 may be coupled to the input interface circuitry 406. In this example, a microphone is used to provide a further degree of control in producing a fan control outputs 218.

Figure 5:
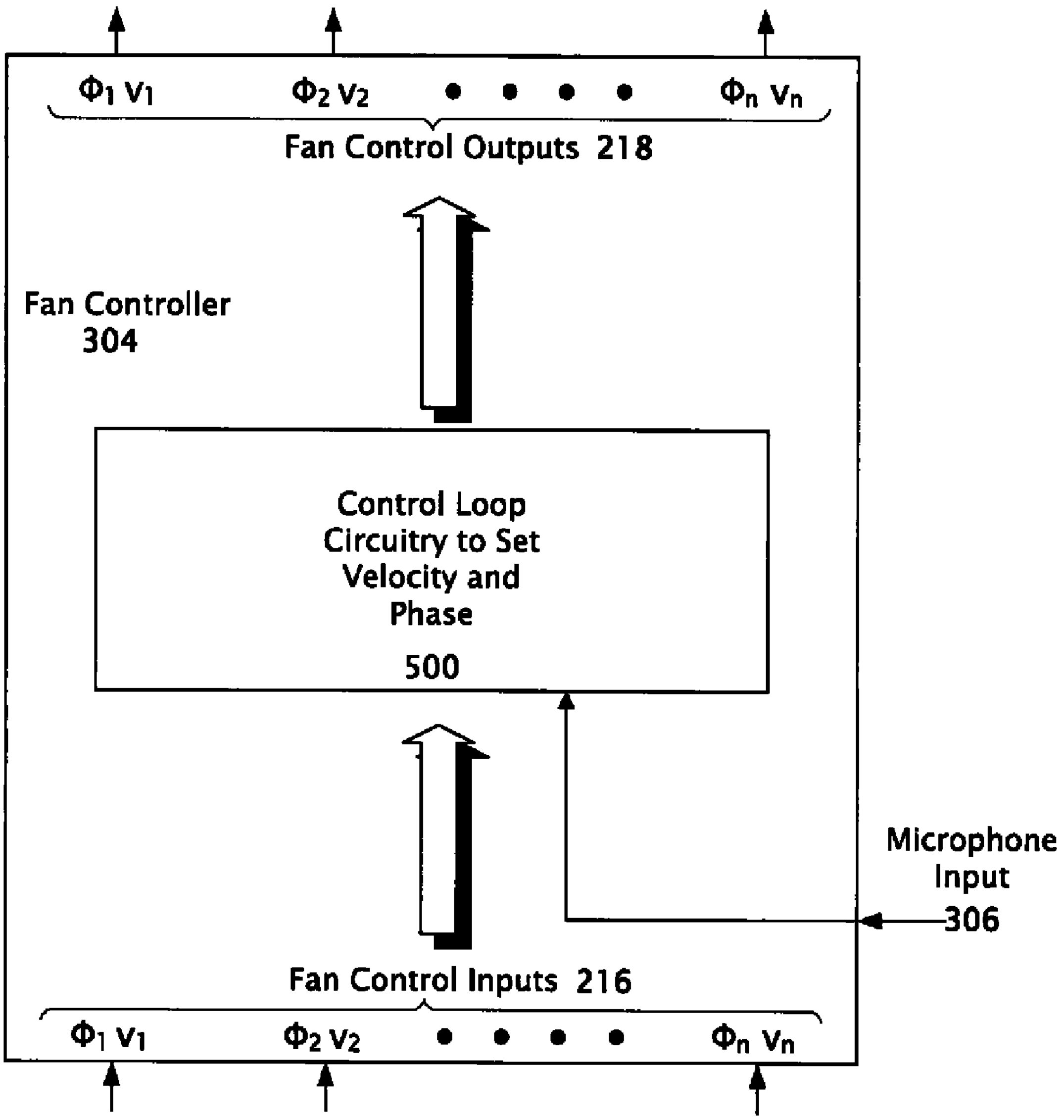
FIG. 5 is a block diagram of an example of a fan controller utilizing control loop circuitry to set fan velocity and phase.

FIG. 5 is a block diagram of an example of a fan controller 304 utilizing control loop circuitry to set fan velocity and phase. In this example, microphone input 306 is coupled to conventional control loop circuitry to set velocity and phase 500. In addition, optional fan control inputs 216 may also be coupled to the control circuitry to set fan velocity and phase 500. The control loop circuitry to set velocity and phase 500, generates suitable fan control outputs 218 that are coupled to the fans being controlled. The controlled loop circuitry to set velocity and phase 500 is conventionally constructed utilizing feedback circuit techniques.

Figure 6:
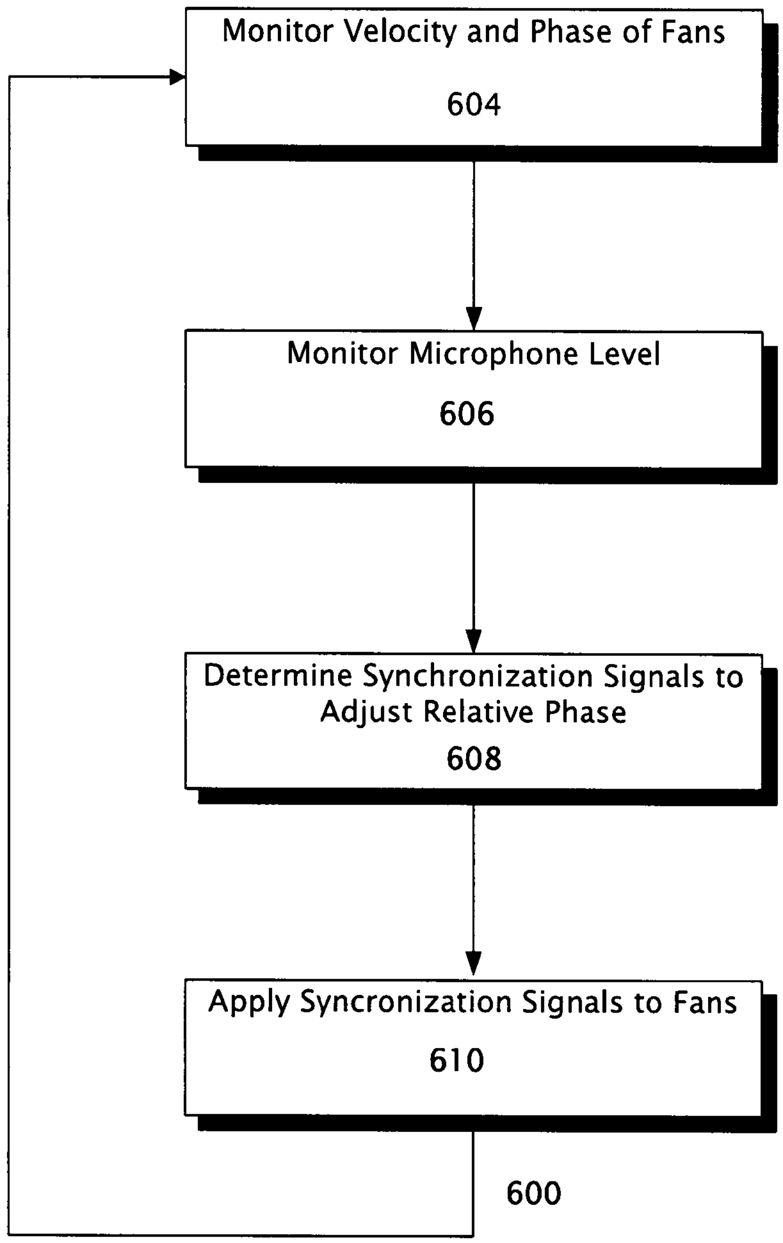
FIG. 6 is block diagram showing a process for reducing audible fan noise that may be executed by an example of the fan controller (of FIG. 5).

FIG. 6 is block diagram showing a process for reducing audible fan noise that may be executed by an example of the fan controller (304 of FIG. 5). First, the velocity and phase of the fans is monitored 604. The signals from the microphone are also monitored 606. Then, the synchronization signals to adjust relative phase are determined 608. Next, the synchronization signals are applied to the fan 610. The process is continuous with the flow control returning to block 604 where the velocity and phase of the fans continue to be monitored.

In an alternative examples, either the velocity or phase of the fans may be monitored. And in a further alternative example, the microphone 606 may be monitored alone.

Figure 7:
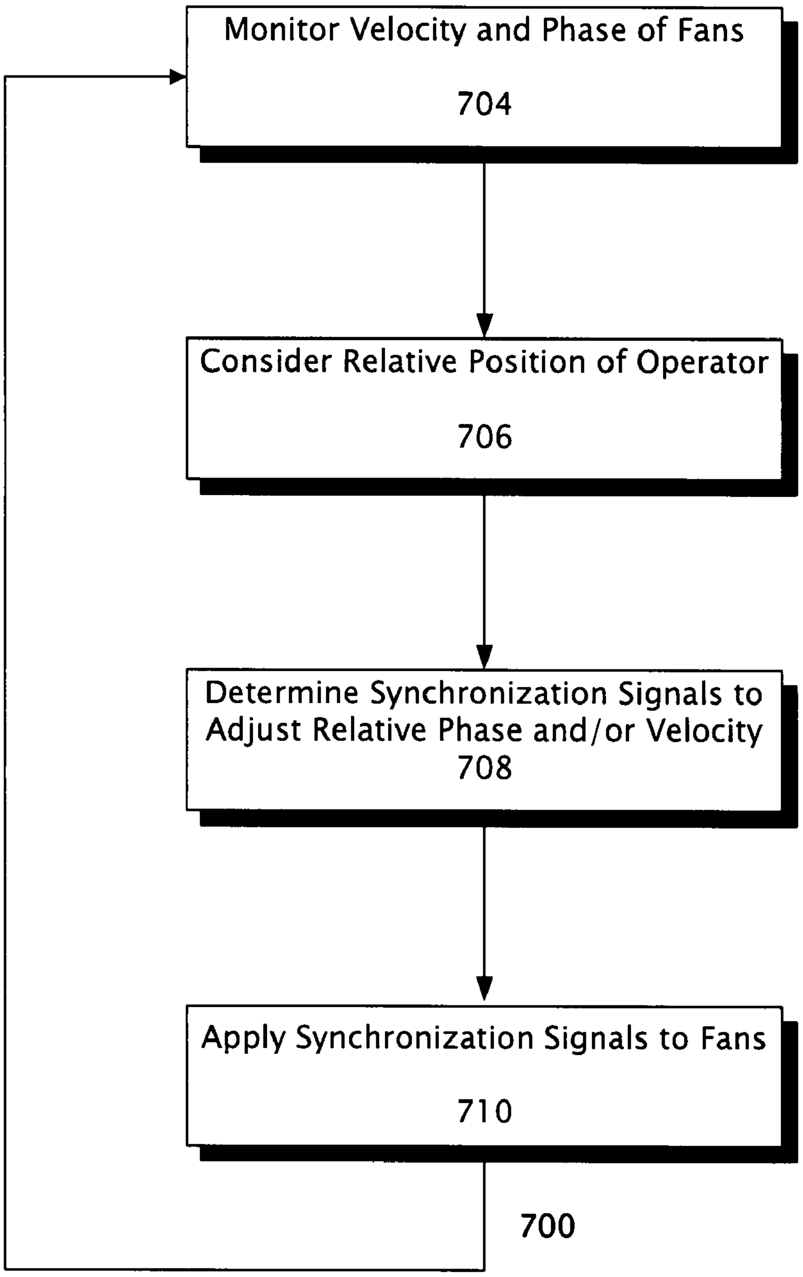
FIG. 7 shows a process for calculating nulls and controlling the fan suitable for application by the fan controller (of FIG. 4).

FIG. 7 shows a process for calculating nulls and controlling the fan suitable for application by the fan controller 214 (of FIG. 4). First, the velocity and phase of the fans may be monitored 704. Next, the distance of the operator to the equipment is inputted and taken into consideration 706. Then, the signals to adjust relative phase and/or velocity are determined 708. The synchronization signals generated are applied to the fans 710. Next, as the process is continuous, process control returns to block 604 where the velocity and phase of the fans may continue to be monitored. In alternative examples, either the velocity or the phase may be monitored and utilized to derive a control signal.

Those skilled in the art will realize that the process sequences described above may be equivalently performed in any order to achieve a desired result. Also, sub-processes may typically be omitted as desired without taking away from the overall functionality of the processes described above.

Those skilled in the art will realize that storage devices utilized to store program instructions can be distributed across a network. Also, a PC may be used to store and execute program instructions to implement the methods described. Those skilled in the art will also realize that by utilizing conventional techniques known to those skilled in the art, that all, or a portion of the software instructions may be carried out by a dedicated circuit, such as a DSP, programmable logic array, or the like.

The invention claimed is:

1. A system for canceling fan noise, comprising:

a plurality of fans, each fan of the plurality of fans generating a fan phase output, and a fan velocity output, and also having a fan phase input and a fan velocity input;

a fan controller having a fan control input coupled to the fan phase output and the fan velocity output of each of the plurality of fans and a fan control output coupled to the fan velocity input and the fan phase input of each of the plurality of fans, such that a local audio null may be produced to minimize fan noise heard by on operator; and an interface operably coupled to the fan controller and configured for receiving an input defining at least one of: a fixed distance from an operator to the plurality of fans and, an angle away from an axis normal to the plurality of fans.

2. A system for canceling fan noise as claimed in claim 1, wherein the fan phase output and the fan velocity output of each of the plurality of fans is determined by utilizing the fixed distance from an operator to the plurality of fans.

3. A system for canceling fan noise as claimed in claim 2, wherein the fan controller includes a processing circuit coupled to the fan control inputs, and coupled to the fan control output.

4. A system for canceling fan noise as claimed in claim 3, wherein the processing circuit includes:

a processor coupled to the fan control inputs and coupled to the fan control outputs; and a memory coupled to the processor.

5. A system for canceling fan noise as claimed in claim 3, wherein the processing circuit is a programmable logic array.

6. A system for canceling fan noise as claimed in claim 3, further comprising:

input interface circuitry having inputs coupled to the fan control inputs and having outputs coupled to an input of the processing circuit; and output interface circuitry having inputs coupled to the processing circuit and having outputs coupled to fan control outputs.

7. A system for canceling fan noise as claimed in claim 1, further comprising: a microphone, the microphone being coupled to the fan controller.

8. A system for canceling fan noise as claimed in claim 7, wherein the fan controller further comprises: a control loop circuit coupled to the microphone, and coupled to the fan control output.

9. A system for canceling fan noise as claimed in claim 8, wherein the control loop circuit is coupled to the fan control inputs.

10. A system for canceling fan noise as claimed in claim 7, wherein the microphone is coupled to the operator.

11. A system for canceling fan noise as claimed in claim 7, wherein the microphone generates a feedback signal to cause the adjustment of a noise output of the plurality of the fans such that a local audio null is produced.

12. A method for reducing fan noise via a fan controller, the method comprising:

receiving an input defining at least one of: a fixed distance from an operator to the plurality of fans and, an angle away from an axis normal to the plurality of fans;

monitoring velocity and phase of a plurality of fans, including: receiving velocity outputs and phase outputs at the fan controller, the velocity outputs and phase outputs being provided to the fan controller from the fans;

monitoring a microphone to determine a noise level associated with the plurality of fans;

determining synchronization signals to adjust the phase and the velocity of the plurality of fans based on the determined noise level; and applying the synchronization signals to the fans for reducing the determined noise level and reducing the fan noise, the synchronization signals including fan velocity inputs and a fan phase inputs.

13. A method for reducing fan noise as claimed in claim 12, wherein the microphone moves with an operator.

14. A method for reducing fan noise as claimed in claim 12, wherein the microphone is continuously monitored.

15. A method for reducing fan noise as claimed in claim 12, wherein determining synchronization signals is performed by a control loop.

16. A method for reducing fan noise as claimed in claim 12, wherein determining synchronization signals is performed by a plurality of control loops.

17. A method of canceling fan noise of a plurality of fans via a fan controller, the method comprising:

receiving an input defining at least one of: a fixed distance from an operator to the plurality of fans and, an angle away from an axis normal to the plurality of fans;

determining a position of an operator according to the input;

determining synchronization signals to adjust a fan phase and a fan velocity of at least one fan included in the plurality of fans, based on the position of an operator; and applying the synchronization signals to the plurality of fans to cancel fan noise of the plurality of fans, the synchronization signals including fan velocity inputs and a fan phase inputs.

18. A method of canceling fan noise as claimed in claim 17, wherein the position of an operator is directly in front of the fans.

19. A method for canceling fan noise as claimed in claim 17, wherein the velocity and phase of the fans is continuously monitored.

* * * * *